United States Patent
Seo et al.

(10) Patent No.: US 6,890,560 B2
(45) Date of Patent: May 10, 2005

(54) NEGATIVELY CHARGED AMPHIPHILIC BLOCK COPOLYMER AS DRUG CARRIER

(75) Inventors: Min-Hyo Seo, Daejeon (KR); In-Ja Choi, Daejeon (KR); Han-Uk Kong, Seoul (KR)

(73) Assignee: Samyang Corporation (KR)

( * ) Notice: Subject to any disclaimer, the term of this patent is extended or adjusted under 35 U.S.C. 154(b) by 0 days.

(21) Appl. No.: 10/104,587

(22) Filed: Mar. 21, 2002

(65) Prior Publication Data

US 2003/0017206 A1 Jan. 23, 2003

(30) Foreign Application Priority Data

Jun. 25, 2001 (KR) .......................................... 2001-36203

(51) Int. Cl.[7] .............................. A61K 9/14; C08L 67/00
(52) U.S. Cl. ....................... 424/486; 424/489; 424/490; 525/415
(58) Field of Search ................................. 424/486, 489, 424/490; 525/542, 88, 58, 61, 186, 408, 543, 411, 423, 415; 528/354, 359

(56) References Cited

U.S. PATENT DOCUMENTS

| | | | |
|---|---|---|---|
| 4,908,155 A | | 3/1990 | Leemans et al. |
| 5,035,972 A | | 7/1991 | El-Sayed et al. |
| 5,420,211 A | * | 5/1995 | Hughes et al. ............... 525/404 |
| 5,469,448 A | * | 11/1995 | Wong et al. ................ 424/9.45 |
| 5,567,410 A | * | 10/1996 | Torchillin et al. ............ 424/9.4 |
| 5,569,448 A | | 10/1996 | Wong et al. |
| 5,783,178 A | | 7/1998 | Kabanov et al. |
| 5,929,177 A | | 7/1999 | Kataoka et al. |
| 5,939,453 A | | 8/1999 | Heller et al. |
| 6,201,065 B1 | | 3/2001 | Pathak |
| 6,267,987 B1 | * | 7/2001 | Park et al. ................... 424/486 |

FOREIGN PATENT DOCUMENTS

EP 0721776 1/1996

OTHER PUBLICATIONS

Yoo et al. "Biodegradable polymeic micelles composed of doxorubicin conjugated PLGA–PEG block copolymer," in Journak of Controlled Release 70 (2001) 63–70.*
R. Langer—New Methods of Drug Delivery, 249 *Science* 1527–1533 (1990).
B. Jeong, et al,—Biodegradable Block Copolymers as Injectable Drug–delivery Systems, 388 *Nature* 860–862 (1997).

* cited by examiner

*Primary Examiner*—Gollamudi S. Kishore
*Assistant Examiner*—Blessing M. Fubara
(74) *Attorney, Agent, or Firm*—Thorpe North & Western LLP

(57) ABSTRACT

The present invention provides an anionic group-containing amphiphilic block copolymer that is biocompatible and biodegradable and, when used as a drug carrier for a cationic drug, provides several advantages such as increased blood concentration and improved stability of the drug.

24 Claims, 11 Drawing Sheets

$^1$H-NMR spectrum of mPEG-PLA-O-SO$_3$

NEGATIVELY CHARGED AMPHIPHILIC BLOCK COPOLYMER AS DRUG CARRIER

CROSS REFERENCE TO RELATED APPLICATIONS

This application claims benefit of Korean patent application No. 2001-36203, filed Jun. 25, 2001.

TECHNICAL FIELD

The present invention relates to a negatively charged polymeric micelle type drug carrier which forms a complex with a positively charged drug. More specifically, the present invention relates to a negatively charged polymeric drug carrier which comprises an A-B type block copolymer wherein A is a hydrophilic polymer block and B is a hydrophobic biodegradable polymer block and wherein one or both ends of the hydrophobic polymer block(B) is covalently bound to one anionic group. The negatively charged biodegradable block copolymer of the present invention forms a complex with the positively charged drug via electrostatic interactions. The anionic copolymers of the present invention can be used in drug delivery and are especially useful for delivery of cationic bioactive agents.

BACKGROUND OF THE INVENTION

Biodegradable polymers are gaining attention as drug delivery systems. R. Langer, New Methods of Drug delivery, 249 Science 1527–1533 (1990); B. Jeong et al., Biodegradable Block Copolymers as Injectable Drug-delivery Systems, 388 Nature 860–862 (1997). Delivering bioactive agents from a biodegradable delivery system is highly desirable because the need for a surgical procedure to remove the delivery system is avoided. Controlled release of bioactive agents can reduce the required frequency of administration by maintaining the concentration of the therapeutic agent at desired levels. One important means of maintaining the proper concentration is by controlling the degradation rate of the biodegradable drug delivery system.

The biodegradable hydrophobic polymers widely used as drug carriers include polylactic acid (PLA), polyglycolic acid (PGA), a copolymer of lactic acid and glycolic acid (PLGA), polycaprolactone (PCL), polyorthoester (POE), polyamino acid (PAA), polyanhydride (PAH), polyphosphazine, polyhydroxybutyric acid (PHB), polydioxanone (PDO), etc. Such polymers have good biocompatibility and the desirable feature of being hydrolyzed and decomposed in a living body to side products which have no toxicity. For these reasons they are widely used as drug carriers. In particular, since these polymers are insoluble in water formulations some drugs are incorporated into the polymer matrix and then implanted in the body in the form of microspheres, nanospheres, films, sheets or rods, whereby the drug is slowly released and exerts a sustained therapeutic effect. In these types of formulations, the polymers themselves are finally decomposed in the body. However, these polymers have a low affinity for water-soluble drugs and it is very difficult to incorporate a large amount of drug into the polymer matrix. Even if the drug is effectively incorporated into the polymer matrix, the problem of initial burst release (which means a phenomenon whereby a large amount of drug is released within the first few hours) may occur when it is implanted into the body.

The A-B, B-A-B, or A-B-A type block copolymers, wherein A is a hydrophilic polymer block and B is a hydrophobic biodegradable polymer block, have been used as drug carriers for the delivery of physiologically active materials in the form of polymeric micelles, nanospheres, microspheres, gels, etc. These block copolymers have desirable properties such as good biocompatibility and the ability to form core-shell type polymeric micelles in an aqueous solution where the core is composed of the hydrophobic blocks and the shell is composed of the hydrophilic blocks. The micellar formulation wherein a poorly water soluble drug can be incorporated into the inside of polymeric micelle to give a micellar solution are good drug carriers for hydrophobic drugs. However, since the drug is incorporated via hydrophobic interaction between the hydrophobic drug and the hydrophobic polymer, the incorporation efficiency of highly hydrophobic drugs is excellent, but water-soluble hydrophilic drugs can hardly be incorporated at all into those polymeric micelles.

Kataoka et al.(EP 721,776 A1) have developed a method for incorporating a charged water-soluble drug into the inside of a polymeric micelle using a block copolymer consisting of a non-charged block and a charged block. The charged block used by Kataoka is a polyamino acid having an ionic side chain, such as polyaspartic acid, polyglutamic acid, polylysine, polyarginine, or polyhistidine. However, they are not biodegradable in a living body. In addition since the charged block may include several functional groups having electric charges, when they are combined inside the molecule via electrostatic binding with a drug having multiple ionic groups, such as peptides or proteins, they may decrease the stability of such drugs.

In view of the foregoing, development of a drug carrier for cationic drug delivery that is biocompatible and biodegradable will be appreciated and desired. Thus, the present invention provides a new type of negatively charged amphiphilic block copolymer that is biocompatible and biodegradable and which can effectively deliver the drug without a decrease in its stability. By forming a complex with a cationic drug via electrostatic interaction, the anionic amphiphilic block copolymer of the present invention can effectively incorporate a water-soluble positively charged drug into the amphiphilic block copolymer. In addition, the block copolymer of the present invention is readily susceptible to metabolic degradation after incorporation and delivery of the drug into the cell.

BRIEF SUMMARY OF THE INVENTION

The present invention provides an anionic group-containing amphiphilic block copolymer that is biocompatible and biodegradable and, when used as a drug carrier for a cationic drug, provides several advantages such as increased blood concentration and improved stability of the drug. The anionic group amphiphilic block copolymer of the present invention is particularly useful for delivering a drug having multiple cationic groups in the molecule, such as a peptide or protein drug, because it will prevent the drug from being decomposed enzymatically in a living body and also improve the stability of the drug by inhibiting the formation of peptide-peptide or protein-protein complexes.

The present invention also provides a drug-copolymer complex wherein a cationic drug is combined via electrostatic binding with the anionic amphiphilic block copolymer of the present invention. Additional features and advantages of the invention will be apparent from the detailed description that follows, taken in conjunction with the accompanying drawings, which together illustrate, by way of example, features of the invention

DETAILED DESCRIPTION

Figure 1:
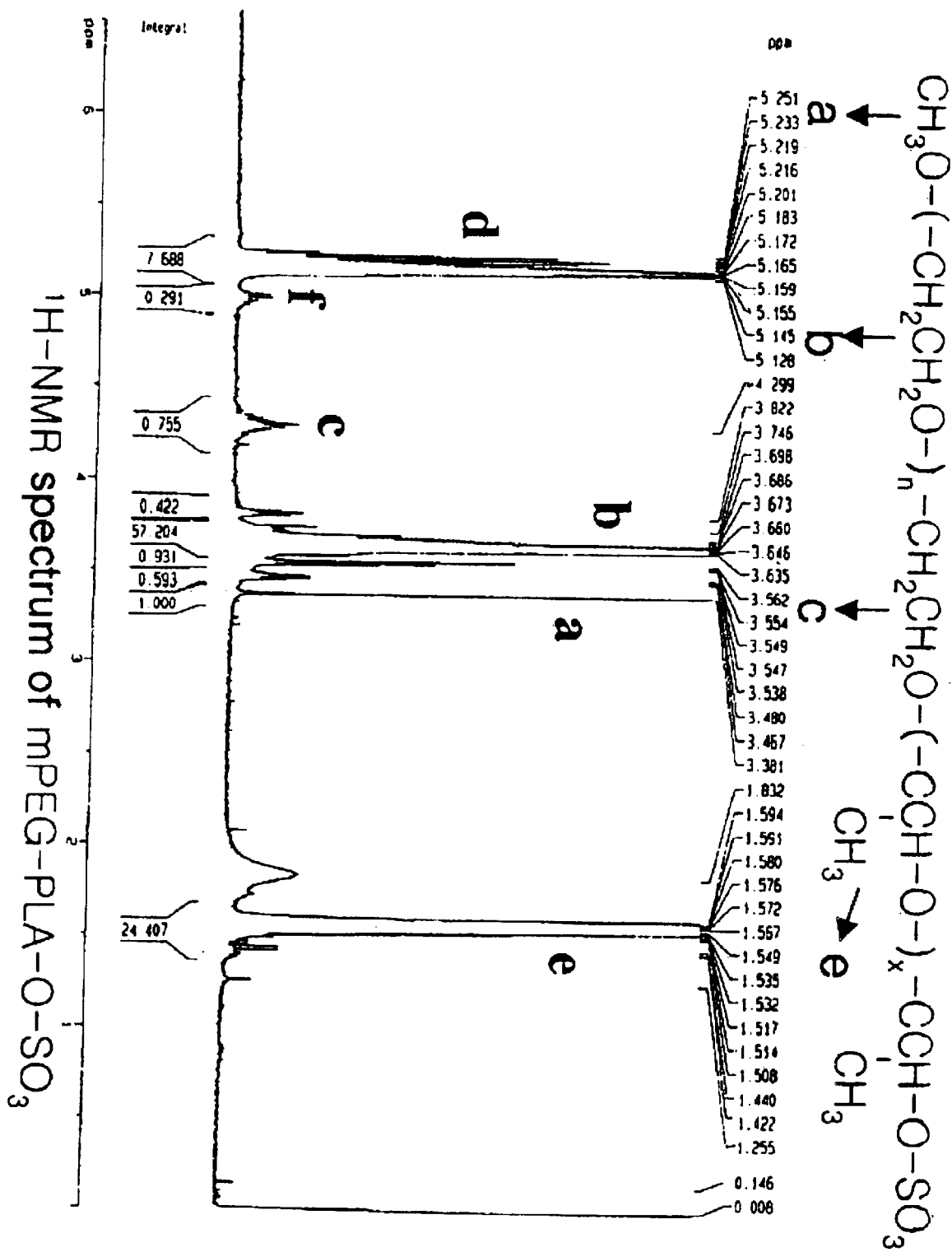
FIG. 1 is an $^1$H-NMR(CDCl$_3$) spectrum of mPEG-PLA-O—SO$_3^-$Na$^+$.

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a functional group" includes reference to two or more of such groups, reference to "a ligand" includes reference to one or more of such ligands, and reference to "a drug" includes reference to two or more of such drugs.

In describing and claiming the present invention, the following terminology will be used in accordance with the definitions set out below.

As used herein, the term "bioactive agent" or "drug" or any other similar term means any chemical or biological material or compound suitable for administration by methods previously known in the art and/or by the methods taught in the present invention and that induce a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anaesthetic effect, or it may be systemic.

As used herein, the term "biodegradable" or "biodegradation" is defined as the conversion of materials into less complex intermediates or end products by solubilization hydrolysis, or by the action of biologically formed entities which can be enzymes and other products of the organism.

As used herein, the term "biocompatible" means materials or the intermediates or end products of materials formed by solubilization hydrolysis, or by the action of biologically formed entities which can be enzymes and other products of the organism and which cause no adverse effects to the body.

"Poly(lactide-co-glycolide)" or "PLGA" shall mean a copolymer derived from the condensation copolymerization of lactic acid and glycolic acid, or, by the ring opening polymerization of α-hydroxy acid precursors, such as lactide or glycolide. The terms "lactide," "lactate," "glycolide" and "glycolate" are used interchangeably.

"Poly(lactide)" or "PLA" shall mean a polymer derived from the condensation of lactic acid or by the ring opening polymerization of lactide. The terms "lactide" and "lactate" are used interchangeably.

"Biodegradable polyesters" refer to any biodegradable polyesters, which are preferably synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydrooxybutyric acids, malic acid, and copolymers thereof.

As used herein, "effective amount" means the amount of a nucleic acid or bioactive agent that is sufficient to provide the desired local or systemic effect and performance at a reasonable risk/benefit ratio as would attend any medical treatment.

As used herein, "peptide", means peptides of any length and includes proteins. The terms "polypeptide" and "oligopeptide" are used herein without any particular intended size limitation, unless a particular size is otherwise stated. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate; and the like.

As used herein, "administering", and similar terms means delivering the composition to the individual being treated such that the composition is capable of being circulated systemically where the composition binds to a target cell and is taken up by endocytosis. Thus, the composition is preferably administered to the individual systemically, typically by subcutaneous, intramuscular, transdermal, oral, transmucosal, intravenous, or intraperitoneal administration. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like. For oral administration, it can be formulated into various forms such as solutions, tablets, capsules, etc.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

The present invention relates to a block copolymer represented by the following formula (1):

A-B-L-X-M$^+$ (1)

Wherein X represents an anionic group, M$^+$ represents H$^+$ or a metal cation, A is a biocompatible hydrophilic polymer, B is a biodegradable hydrophobic polymer, and L represents a linker selected from the group consisting of —O—, —NH—, —S— and —COO—.

The present invention also provides to a drug-polymer complex comprising a block copolymer represented by the formula (1) and a positively charged drug wherein the cationic drug is complexed with the anionic amphiphilic block copolymer via electrostatic binding.

The negatively charged polymer according to the present invention comprises an A-B amphiphilic block copolymer consisting of hydrophilic blocks(A) and biodegradable hydrophobic blocks(B) wherein the one or both terminal ends of the hydrophobic blocks(B) are capped, through a linker, with one anionic group. Examples of the block copolymers include A-B-L-X wherein A is a hydrophilic block, B is a biodegradable hydrophobic block, L is a linker as defined above and X is an anionic group.

The hydrophilic block(A) is a biocompatible, water-soluble and non-ionic polymer segment which includes a polyalkyleneglycol such as polyethyleneglycol, poly(ethylene-co-propylene)glycol, etc., polyalkyleneoxide, polyvinylpyrrolidone, a polysaccharide, polyacrylamide, polymethacrylamide, polyvinylalcohol, and derivatives thereof, preferably polyethyleneglycol, poly(ethylene-co-propylene)glycol, polyvinylpyrrolidone, polyacrylamide, polyvinylalcohol, and derivatives thereof, more preferably polyethyleneglycol and derivatives thereof.

Furthermore, the biocompatible hydrophilic block (A) includes derivatives having a high molecular weight wherein said water-soluble and non-ionic polymer segments having a low molecular weight are combined together via degradable linkers. The hydrophilic block A can be synthesized as in Reaction Scheme 1:

Reaction Scheme 1

wherein
Z represents a water-soluble polymer having a molecular weight of up to 5,000 Daltons,
Y represents HOOC—(CH$_2$)$_m$—COOH or O=C=N—(CH$_2$)$_m$—N=C=O(wherein m denotes an integer of 0 to 10), and
n denotes an integer of 2 to 100.

The hydrophilic block(A) preferably has a number average molecular weight of from 100 to 100,000 Daltons, and may also have any type of structure such as a single chain, a branch, etc. Examples include PEG-OOC—(CH$_2$)$_m$—COO-PEG or PEG-[OOC—(CH$_2$)$_m$—COO-PEG]$_{10}$—OOC—(CH$_2$)$_m$—COO-PEG wherein the molecular weight of PEG is up to 5,000 Daltons.

In the negatively charged block copolymer according to the present invention, the biodegradable hydrophobic block (B) is preferably a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydrooxybutyric acids, malic acid, and copolymers thereof. More preferably, the biodegradable polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, and copolymers thereof.

The hydrophobic B-blocks are utilized because of their biodegradable, biocompatible, and solubilization properties. The in vitro and in vivo degradation of these hydrophobic, biodegradable polyester B-blocks is well understood and the degradation products are naturally occurring compounds that are readily metabolized and/or eliminated by the patient's body.

Examples of biodegradable hydrophobic B polymer blocks include poly(α-hydroxy acid) or derivatives thereof such as polylactic acid(PLA), polyglycolic acid(PGA), a copolymer of polylactic acid and glycolic acid(PLGA) and copolymers thereof; polyesters or derivatives thereof such as polyorthoester(POE), polyanhydride (PAH), polycaprolactone(PCL), poly(dioxan-2-one)(PDO), polyhydroxybutyric acid(PHB), a copolymer of lactic acid and dioxan-2-one(PLDO), a copolymer of caprolactone and dioxan-2-one(PCDO), and copolymers thereof, polyphosphazine. Examples of the preferred biodegradable hydrophobic B polymer blocks include poly(α-hydroxy acid) or derivatives thereof such as hydrolyzable polylactic acid (PLA), polyglycolic acid(PGA), a copolymer of polylactic acid and glycolic acid(PLGA), and copolymers thereof; polyester or derivatives thereof such as polyorthoester (POE), polyanhydride(PAH), polycaprolactone(PCL), poly(dioxan-2-one)(PDO), poly-hydroxybutyric acid(PHB), a copolymer of lactic acid and dioxan-2-one(PLDO), a copolymer of caprolactone and dioxan-2-one(PCDO), and copolymers thereof. More preferably, polylactic acid(PLA), polyglycolic acid(PGA), polycaprolactone, poly(dioxan-2-one), a copolymer of polylactic acid and glycolic acid (PLGA), or copolymers thereof.

The hydrophobic block(B) preferably has a number average molecular weight of from 100 to 100,000 Daltons, and more preferably 500 to 50,000 Daltons.

The anionic group(X) in the negatively charged block copolymer, according to the present invention, is attached at the end of the hydrophobic block(B) by means of a linker L. If the terminal end of the hydrophobic block(B) is a functional —OH, —NH$_2$, —SH or —COOH group, the anionic group is directly linked to the hydrophobic block(B) with the functional group providing the linker L. If not, the hydrophobic B block may be appropriately derivatized such that it may be linked to the anionic group through a suitable linker(L), such as, —O—, —NH—, —S— or —COO—. In the present invention, only one anionic group(X) can be present at the end of a B hydrophobic polymer block.

However, if the polymer terminates at each end with a B polymer block, there can be an anion X attached through a linker L at each end of the polymer. The anionic group is selected from those that are negatively charged in aqueous solutions, preferably from a group consisting of $—SO_3{}^-$, $—PO_3{}^{2-}$, $=PO_2{}^-$ and $—CO—(CH_2)_z—COO^-$(wherein, z denotes an interger of 0 to 4, and if X is $>PO_2{}^-$, the anionic group is combined with two carbon atoms).

M includes $H^+$ and cations, preferably a mono- or divalent metal ion, more preferably $Li^+$, $Na^+$, $K^+$, $Ca^{2+}$, $Mg^{2+}$, $Zn^{2+}$ and $Cu^{2+}$.

Therefore, the negatively charged block copolymer according to the present invention may have the following formula 1a:

$$\text{A-B-L-X}^-\,{}^+\text{M} \quad (1a)$$

wherein
A is a biocompatible hydrophilic polymer block,
B is a biodegradable hydrophobic polymer block
L is a linker selected from the group consisting of —O—, —NH—, —S—, and COO—,
X is $—SO_3{}^-$, $—PO_3{}^{2-}$, $=PO_2{}^-$ or $—CO—(CH_2)_z—COO^-$ (where, z denotes an integer of 0 to 4, and if X is $>PO_2{}^-$, the anionic group is combined with two carbons), and
M is a mono- or divalent metal ion.

More specifically, when L is —O—, the negatively charged block copolymer of the present invention may have the following formula:

$$\text{A-B-O—SO}_3{}^-\text{M}^+$$

$$\text{A-B-O—PO}_3{}^{2-}\text{2M}^+$$

$$\text{A-B-O—CO—(CH}_2)_z\text{—COO}^-\text{M}^+$$

$$(\text{A-B-O})_2\text{—PO}_2{}^-\text{M}^+$$

wherein
A is methoxypolyethyleneglycol, polyethyleneglycol, polyvinylpyrrolidone, polyacrylamide, poly(ethylene-co-propylene)glycol, a polyvinylalcohol or a polysaccharide,
B is polylactide, polyglycolide, polycaprolactone, polydioxan-2-one, polyanhydride, poly(lactic-co-glycolide), poly(lactic-co-caprolactone), or poly (lactic-co-dioxan-2-one), etc.,
M is $Li^+$, $Na^+$ or $K^+$, and
z is an integer of 0 to 4.

The negatively charged block copolymer of the present invention is prepared by a two-step reaction which comprises synthesizing type A-B block copolymers consisting of non-ionic hydrophilic blocks(A) and hydrophobic blocks (B), and then introducing an anionic group onto the terminal end of an appropriately derivatized hydrophobic block(B).

1) Introduction of sulfate groups $$\text{A-B-OH} \rightarrow \text{A-B-O—SO}_3{}^-\text{Na}^+$$

In the above scheme, L is —O—, X is $SO_3{}^-$ and M is $Na^+$
Type A-B block copolymers are reacted with a sulfur trioxide pyridine complex ($C_5H_5NSO_3$), treated with an aqueous acidic solution, neutralized, dialyzed, and then lyophilized. The order of neutralization and dialysis may be reversed depending on the reagent used.

2) Introduction of phosphate groups $$\text{A-B-OH} \rightarrow \text{A-B-O—PO}_3{}^{2-}\text{2Na}^+$$

In the above scheme L is —O—, X is $PO_3{}^{2-}$ and M is $2Na^+$

Type A-B block copolymers are reacted with excess phosphorus oxychloride ($POCl_3$), treated with an aqueous acidic solution, neutralized, dialyzed, and then lyophilized.

3) Introduction of carboxyl groups $$\text{A-B-OH} \rightarrow \text{A-B-O—CO—(CH}_2)_z\text{—COO}^-\text{Na}^+\text{(z is an interger of 0 to 4)}$$

In the above scheme L is —O— X is $CO—(CH_2)_z—COO^-$ (where z is an integer of 0 to 4) and M is $Na^+$.

Type A-B block copolymers are reacted with a dicarboxylic acid dichloride such as oxalyl dichloride, malonyl dichloride, succinyl dichloride, glutaryl dichloride, adipic dichloride, etc., treated with an aqueous acidic solution, neutralized, dialyzed, and then lyophilized.

The negatively charged block copolymer of the present invention may form a polymeric micelle, nanoparticle or gel by incorporating the water-soluble drug, having a cationic group, into the inside of the core of the core-shell type drug carrier via electrostatic binding, whereby the concentration in blood of the drug may be increased. Furthermore, peptide or protein drugs may be combined with the negatively charged block copolymer of the present invention via electrostatic binding in the form of one peptide or protein molecule being surrounded by several block copolymers. In this case, decomposition of the peptide or protein by enzymatic action in a living body may be prevented, as well as the stability of the drug may be improved by the prevention of complex formation between protein-protein or peptide-peptide. The release rate of drug from the negatively charged block copolymer of the present invention may be controlled by adjusting the molecular weight of the hydrophobic block (B).

The drug-copolymer complex of the present invention should be understood to include such forms as polymeric micelles, nanoparticles and gels, etc. wherein the anionic group of the negatively charged block copolymer is electrostatically combined with the cationic group of the positively charged drug to form an ionic complex, which is to be converted into the aforementioned forms in aqueous solution. At least one negatively charged block copolymer is combined with one molecule of drug in the drug-copolymer complex. This type of drug-copolymer complex may increase the concentration and half life of the drug in blood, improve the stability of an unstable drug, and retard the enzymatic decomposition of the drug in a living body, particularly peptide or protein drugs. If a drug contains a large number of cationic groups in the molecule, such as peptide or protein drugs, several block copolymer molecules are electrostatically combined with the drug molecule, whereby the formation of complexes between drugs is prevented, and thus the stability of the drug is improved.

Drugs that can be used in the present invention include those having cationic groups in the molecule in aqueous solutions, particularly peptide and protein drugs containing one or more amino groups. Examples include anti-cancer agents, antibiotics, anti-emetic agents, antiviral agents, anti-inflammatory and analgesic agents, anesthetic agents, anti-ulceratives, agents for treating hypertension, agents for treating hypercalcemia, agents for treating hyperlipidemia, etc., each of which has at least one primary, secondary or tertiary amine group in the molecule, preferably, peptides, proteins or enzymes such as insulin, calcitonin, growth hormone, granulocyte colony-stimulating factor(G-CSF), erythropoietin (EPO), bone morphogenic protein (BMP), interferon, interleukin, platelet derived growth factor (PDGF), vascular endothelial growth factor (VEGF), fibroblast growth factor (FGF), nerve growth factor (NGF), urokinase, etc. can be mentioned.

In the process for preparing the drug-block copolymer complex of the present invention, the drug may be incorporated into the inside of the block copolymer by way of simply mixing the positively charged drug and the negatively charged block copolymer in an aqueous solution; or by dissolving the positively charged drug and the negatively charged block copolymer in organic solvents such as ethanol, etc., evaporating the solvent, and dissolving the resulting mixture in an aqueous solution. As stated above, it is another characteristic of the present invention that a special method is not required for incorporating the positively charged drug into the inside of the negatively charged block copolymer.

The drug-block copolymer complex according to the present invention can be administered through blood, muscle, subcutaneous tissue, bone, local tissue, or administered orally or nasally. It can be formulated into various forms such as solutions, injectable suspensions, tablets, capsules, etc.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLES

The following preparations illustrate synthesis of type A-B block copolymers consisting of a hydrophilic polymer segment (A) and a hydrophobic polymer segment (B).

Preparation 1

Synthesis of Monomethoxypolyethyleneglycol-polylactide(mPEG-PLA) Block Copolymers 5.0 g of monomethoxypolyethyleneglycol(Molecular weight: 2,000 Daltons) was introduced into a two-neck, 100 ml round-bottomed flask, and heated to 100° C. for 2–3 hours under reduced pressure(1 mmHg) to remove the moisture. The inside of the reaction flask was filled with dry nitrogen and then the catalyst, stannous octoate (Sn(Oct)$_2$) dissolved in toluene, was added in an amount of 1.0 mol %(10.13 mg, 0.025 mmole) with respect to the monomethoxypolyethyleneglycol. After stirring for 30 minutes, the mixture was heated to 110° C. for 1 hour under reduced pressure(1 mmHg) to evaporate the toluene which was used to dissolve the catalyst. 5 g of purified lactide was added thereto and the resulting mixture was heated to 130° C. for 12 hours. The block copolymer thus produced was dissolved in ethanol and then added to diethylether to precipitate the block copolymer. The block copolymer thus obtained was dried for 48 hours in a vacuum oven. The molecular weight of the resulting block copolymer (mPEG-PLA) was measured as 2,000–1,765 Daltons

Preparation 2

Synthesis of Monomethoxypolyethyleneglycol-poly(lactic-co-glycolide)(mPEG-PLGA) Block Copolymers 5.0 g of monomethoxypolyethyleneglycol(Molecular weight: 5,000 Daltons) was reacted with 3.72 g of lactide and 1.28 g of glycolide in the presence of stannous octoate at 120° C. for 12 hours according to the same manner as in Preparation 1, to give the title block copolymer. The molecular weight of the resulting block copolymer (mPEG-PLGA) was measured as 5,000–4,500 Daltons.

Preparation 3

Synthesis of Monomethoxypolyethyleneglycol-poly(lactic-co-paradioxan-2-one)(mPEG-PLDO) Block Copolymers 7.0 g of monomethoxypolyethyleneglycol(Molecular weight: 12,000 Dalton) was reacted with 4.47 g of lactide and 2.71 g of paradioxan-2-one in the presence of stannous octoate at 110° C. for 12 hours according to the same manner as in Preparation 1, to give the title block copolymer. The molecular weight of the resulting block copolymer (mPEG-PLDO) was measured as 12,000–10,000 Daltons.

Preparation 4

Synthesis of monomethoxypolyethyleneglycol-polycaprolactone (mPEG-PCL) Block Copolymers 7.0 g of monomethoxypolyethyleneglycol(Molecular weight: 12,000 Dalton) was reacted with 3.0 g of ε-caprolactone in the presence of stannous octoate at 130° C. for 12 hours according to the same manner as in Preparation 1, to give the title block copolymer. The molecular weight of the resulting block copolymer (mPEG-PCL) was measured as 12,000–5,000 Daltons.

Table 1 is a summary of the results of the above preparation

TABLE 1

| Preparation | Block copolymer | Number Average Molecular Weight (Daltons) |
|---|---|---|
| 1 | mPEG-PLA-OH | 2,000–1,765 |
| 2 | mPEG-PLGA-OH | 5,000–4,500 |
| 3 | mPEG-PLDO-OH | 12,000–10,000 |
| 4 | mPEG-PCL-OH | 12,000–5,000 |

The following examples illustrate synthesis of type A-B block copolymers containing an anionic group.

Example 1

Synthesis of methoxypolyethyleneglycol-polylactide Containing Sulfate Group(—SO$_3^-$Na$^+$) (mPEG-PLA-O—SO$_3^-$Na$^+$)

The block copolymer prepared in Preparation 1, and having an —OH group at the terminal end of the PLA (hydrophobic B) block was reacted with sulfur trioxide pyridine to give the title block copolymer.

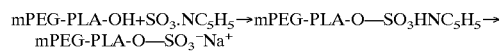

mPEG-PLA-OH+SO$_3$.NC$_5$H$_5$→mPEG-PLA-O—SO$_3$HNC$_5$H$_5$→mPEG-PLA-O—SO$_3^-$Na$^+$ 7 g of methoxypolyethyleneglycol-polylactide(mPEG-PLA, 2,000–1,765) and 0.89 g of sulfur trioxide pyridine (SO$_3$.NC$_5$H$_5$) were dissolved in 10 ml of DMF. The resulting solution was introduced into a 100 ml volume flask and reacted at 60±10° C. for 5 hours. The reaction product was diluted with distilled water, dialyzed, neutralized by an aqueous sodium hydrogen carbonate solution, and then lyophilized to give 5.4 g of the title block copolymer. FIG. 1 is an $^1$H-NMR spectrum(CDCl$_3$) of the block copolymer thus obtained.

Examples 2 to 4

Introduction of a Sulfate Group(—SO$_3^-$Na$^+$)

Each of the block copolymers prepared in Preparations 2 to 4 were reacted with sulfur trioxide pyridine according to the same manner as in Example 1 to give copolymers containing a sulfate group. The block copolymers containing a sulfate group as prepared in Examples 1 to 4 are represented in the following Table 2.

TABLE 2

| Ex. | Block copolymer | Number Average Molecular Weight (Dalton) | |
|---|---|---|---|
| | | A | B |
| 1 | mPEG-PLA-O—SO$_3^-$Na$^+$ | 2,000 | 1,765 |
| 2 | mPEG-PLGA-O—SO$_3^-$Na$^+$ | 5,000 | 4,500 |
| 3 | mPEG-PLDO-O—SO$_3^-$Na$^+$ | 12,000 | 10,000 |
| 4 | mPEG-PCL-O—SO$_3^-$Na$^+$ | 12,000 | 5,000 |

Example 5

Synthesis of Methoxypolyethyleneglycol-polylactide Containing Phosphate Group(—PO$_3^{2-}$2Na$^+$) (mPEG-PLA-O—PO$_3^{2-}$2Na$^+$)

Figure 2:
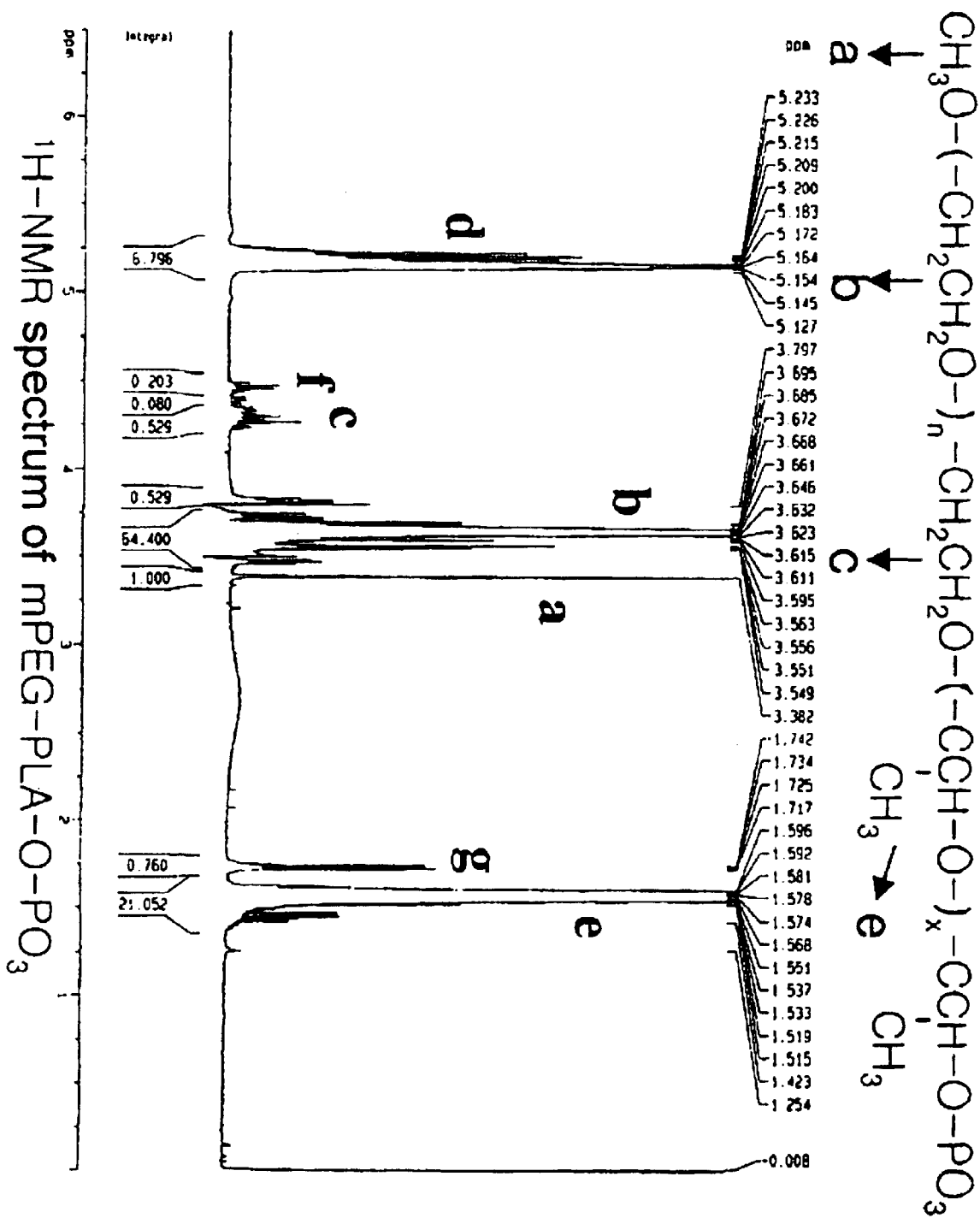
FIG. 2 is an $^1$H-NMR(CDCl$_3$) spectrum of mPEG-PLA-O—PO$_3^{2-}$2Na$^+$.

The block copolymer prepared in Preparation 1 was reacted with phosphorus oxychloride(POCl$_3$) to give the title block copolymer.

mPEG-PLA-OH+POCl$_3$→mPEG-PLA-O—POCl$_2$→mPEG-PLA-O—PO$_3^{2-}$2Na$^+$ 7 g of methoxypolyethyleneglycol-polylactide(mPEG-PLA, 2,000–1,765) and 2.85 g of phosphorus oxychloride (POCl$_3$) were dissolved in chloroform, 1 ml of pyridine was added thereto, and the mixture was reacted at 30±5° C. for 12 hours. The resulting solution was added to diethylether to precipitate block copolymer. The precipitated block copolymer was dissolved in distilled water, neutralized by an aqueous sodium hydrogen carbonate solution, dialyzed, and then lyophilized to give 6.7 g of the title block copolymer. FIG. 2 is an $^1$H-NMR spectrum (CDCl$_3$) of the block copolymer thus obtained.

Examples 6 to 9

Introduction of a Phosphate Group(—PO$_3^{2-}$2Na$^+$)

Each of the block copolymers prepared in Preparations 2 to 4 were reacted with phosphorus oxychloride according to the same manner as in Example 5 to give copolymers containing a phosphate group. The block copolymer as prepared in Examples 5 to 8 are represented in the following Table 3.

TABLE 3

| Ex. | Block copolymer | Number Average Molecular Weight | |
|---|---|---|---|
| | | A | B |
| 5 | mPEG-PLA-O—PO$_3^{2-}$2Na$^+$ | 2,000 | 1,765 |
| 6 | mPEG-PLGA-O—PO$_3^{2-}$2Na$^+$ | 5,000 | 4,500 |
| 7 | mPEG-PLDO-O—PO$_3^{2-}$2Na$^+$ | 12,000 | 10,000 |

Example 9

Synthesis of Methoxypolyethyleneglycol-polylactide Containing a Carboxyl Group(—COO$^-$Na$^+$)

The block copolymer prepared in Preparation 1 was reacted with dicarboxylic acid dichloride to give the title block copolymer.

wherein z is an integer of 0 to 4.

Figure 3:
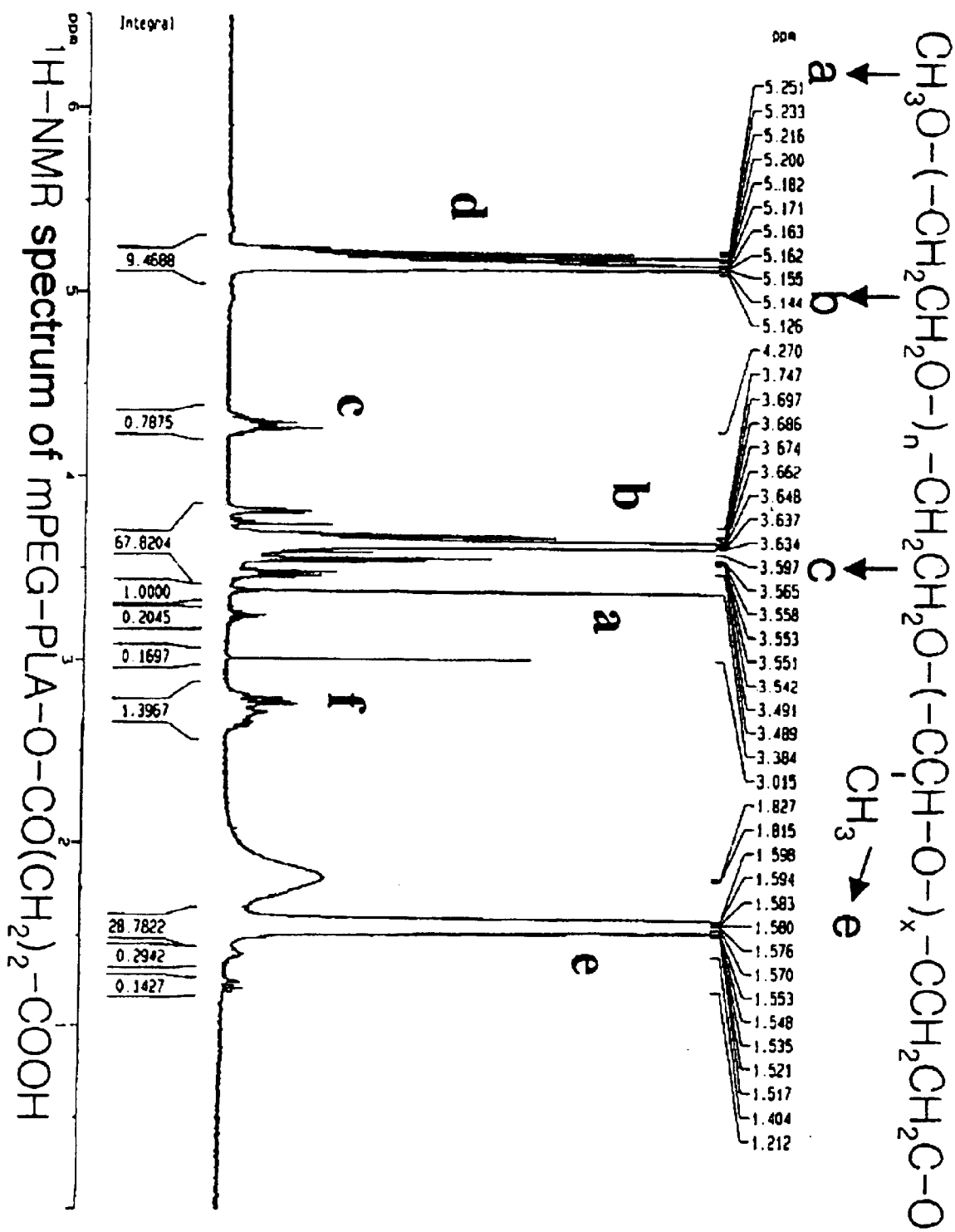
FIG. 3 is an $^1$H-NMR(CDCl$_3$) spectrum of mPEG-PLA-O—CO(CH$_2$)$_2$COO$^-$Na$^+$.

7 g of methoxypolyethyleneglycol-polylactide(mPEG-PLA, 2,000–1,765) and 10 ml of succinyl dichloride(Cl—CO(CH$_2$)$_2$CO—Cl) were dissolved in chloroform, 1 ml of pyridine was added thereto, and the mixture was reacted at 60±5° C. for 12 hours. The resulting solution was added to diethylether to precipitate the block copolymer. The precipitated the block copolymer was dissolved in distilled water, neutralized by an aqueous sodium hydrogen carbonate solution, dialyzed, and then lyophilized to give 5.9 g of the title block copolymer. FIG. 3 is an $^1$H-NMR spectrum (CDCl$_3$) of the block copolymer thus obtained.

Examples 10 to 12

Introduction of a Carboxyl Group (—COO$^-$Na$^+$)

Each of the block copolymers prepared in Preparations 2 to 8 were reacted with succinyl dichloride according to the same manner as in Example 17 to give copolymers containing a carboxyl group. The block copolymers as prepared in Examples 9 to 12 are represented in the following Table 4.

TABLE 4

Example 13: Formation of a doxorubicin hydrochloride-containing

| Ex. | Block copolymer | Number Average Molecular Weight (Dalton) | |
|---|---|---|---|
| | | A | B |
| 9 | mPEG-PLA-O—CO(CH$_2$)$_2$COO$^-$Na$^+$ | 2,000 | 1,765 |
| 10 | mPEG-PLGA-O—CO(CH$_2$)$_2$COO$^-$Na$^+$ | 5,000 | 4,500 |
| 11 | mPEG-PLDO-O—CO(CH$_2$)$_2$COO$^-$Na$^+$ | 12,000 | 10,000 |
| 12 | mPEG-PCL-O—CO(CH$_2$)$_2$COO$^-$Na$^+$ | 12,000 | 5,000 | mPEG-PLA-O—SO$_3^-$Na$^+$ Polymeric Micelle mPEG-PLA-O—SO$_3^-$Na$^+$(10 mg) as prepared in Example 1 and doxorubicin hydrochloride(1 mg) were dissolved in distilled water to give the title polymeric micelle.

Example 14

Formation of a Minocyclin Hydrochloride-Containing mPEG-PLA-O—SO$_3^-$Na$^+$ Polymeric Micelle mPEG-PLA-O—SO$_3^-$Na$^+$(20 mg) as prepared in Example 1 and minocyclin hydrochloride(5 mg) were dissolved in distilled water to give the title polymeric micelle.

Example 15

Formation of a Minocyclin Hydrochloride-Containing mPEG-PLA-O—PO$_3^{2-}$2Na$^+$ Polymeric Micelle mPEG-PLA-O—PO$_3^{2-}$2Na$^+$(20 mg) as prepared in Example 5 and minocyclin hydrochloride(5 mg) were dissolved in distilled water to give the title polymeric micelle.

Example 16

Formation of a Minocyclin Hydrochloride-Containg mPEG-PLA-O—CO(CH$_2$)$_2$COO$^-$Na$^+$ Polymeric Micelle mPEG-PLA-O—CO(CH$_2$)$_2$COO$^-$Na$^+$(40 mg) as prepared in Example 9 and minocyclin hydrochloride(5 mg) were dissolved in distilled water to give the title polymeric micelle.

Example 17

Formation of a Complex of Human G-CSF and mPEG-PLA-O—SO$_3^-$Na$^+$ mPEG-PLA-O—SO$_3^-$Na$^+$(50 mg) as prepared in Example 1 and G-CSF (filgrastim)(1 mg) were dissolved in distilled water to give the title polymeric micelle type-complex.

Example 18

Formation of a Complex of Human Growth Hormone (hGH) and mPEG-PLA-O—SO$_3^-$Na$^+$ mPEG-PLA-O—SO$_3^-$Na$^+$(50 mg) as prepared in Example 1 and hGH(1 mg) were dissolved in distilled water to give the title polymeric micelle type-complex.

Comparative Example 1 mPEG-PLA-OH(20 mg) as prepared in Preparation 1, which does not contain an anionic group, and minocyclin hydrochloride(5 mg) were dissolved in distilled water.

Comparative Example 2 mPEG-PLA-OH(10 mg) as prepared in Preparation 1, which does not contain an anionic group, and doxorubicin hydrochloride(1 mg) were dissolved in distilled water.

Comparative Example 3 mPEG-PLA-OH(50 mg) as prepared in Preparation 1, which does not contain an anionic group, and G-CSF(1 mg) were dissolved in distilled water.

Experiment 1

Confirmation on Whether Drug-Block Copolymer Complex is Formed

Figure 4:
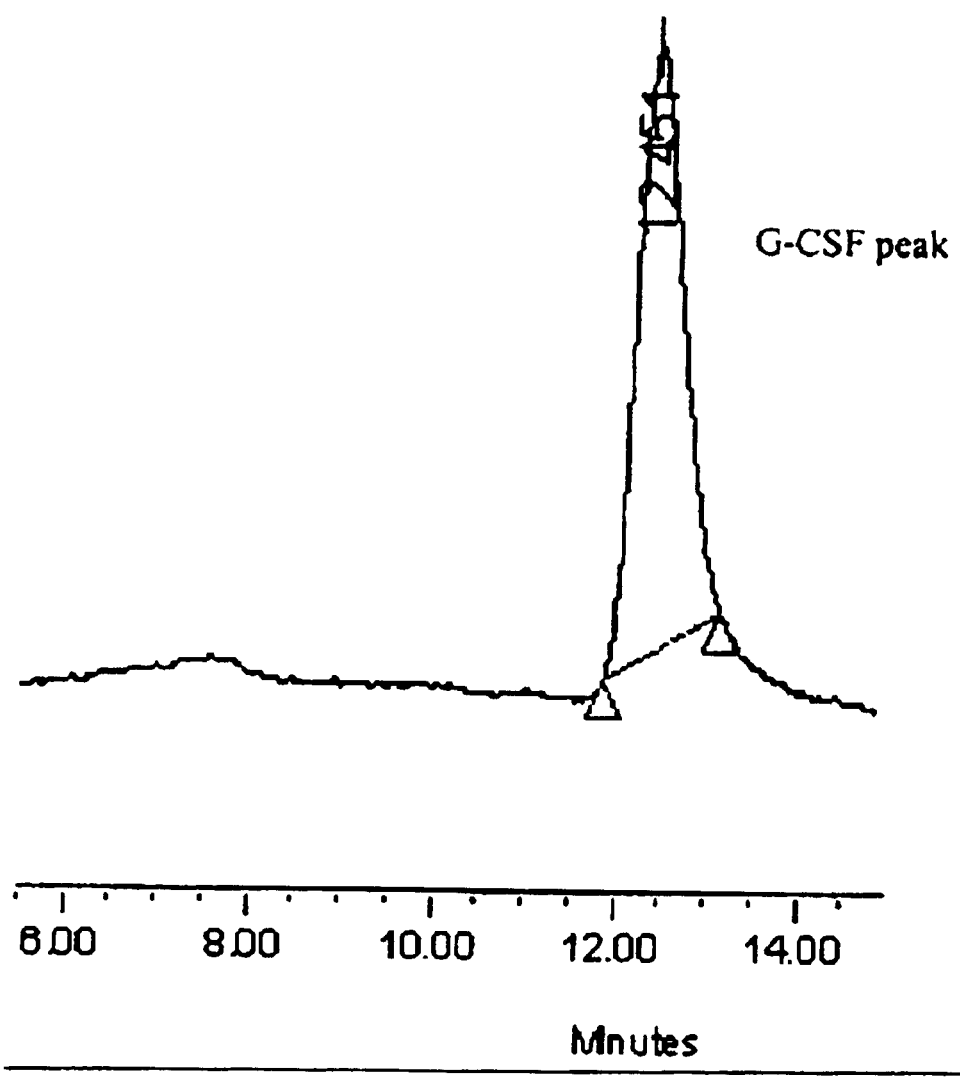
FIG. 4 is a liquid chromatogram of human G-CSF by size exclusive chromatography.
Figure 5:
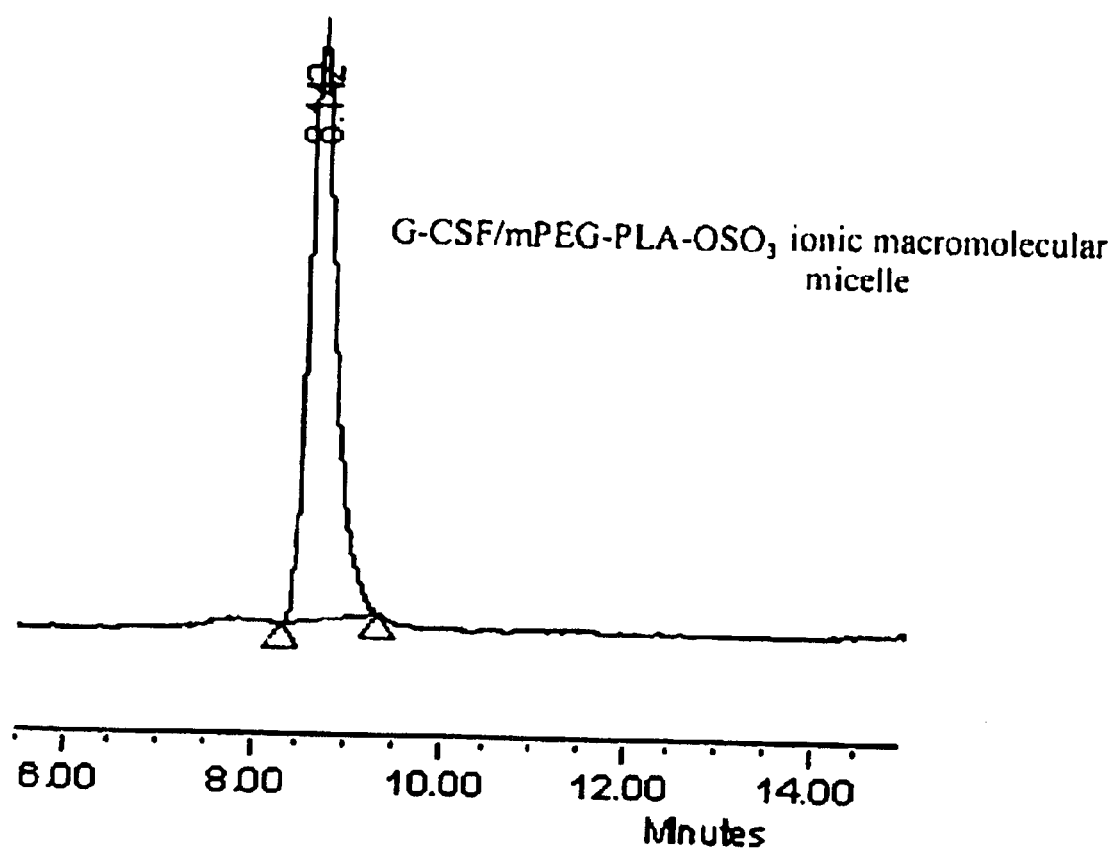
FIG. 5 is a liquid chromatogram of a complex of human G-CSF and mPEG-PLA-O—SO$_3^-$Na$^+$ by size exclusive chromatography.
Figure 6:
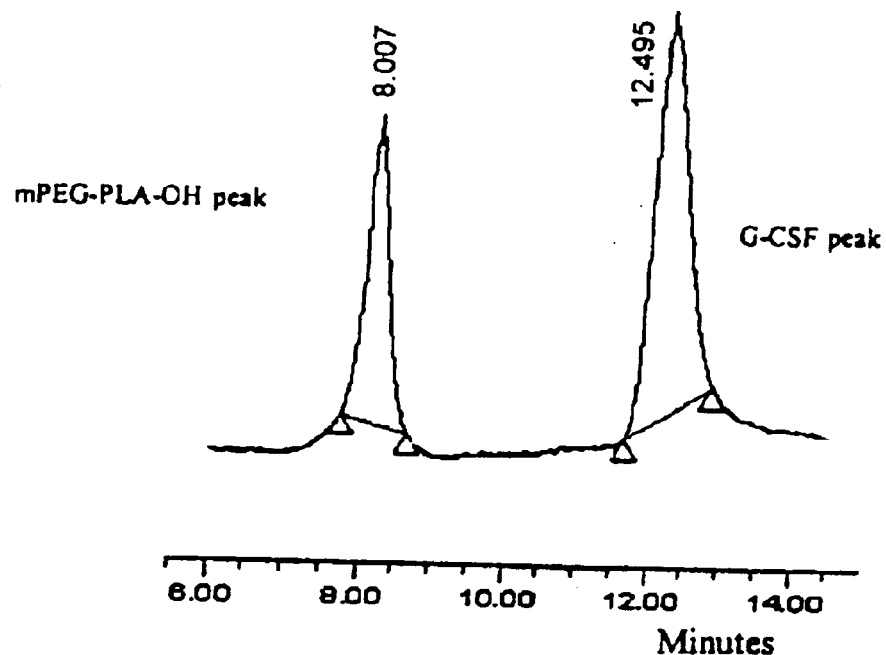
FIG. 6 is a liquid chromatogram of a mixture of human G-CSF and mPEG-PLA-OH by size exclusive chromatography.

Human G-CSF(filgrastim) was analyzed by a size exclusive chromatography column(Pharmacia, Superdex HR 75) (Concentration of human G-CSF 50 µg/ml, injection amount 100 liters, mobile phase pH 7.4 PBS, flow rate 1 ml/min). Furthermore, the polymeric micelle solutions of Example 17 and Comparative Example 3 were analyzed according to the same manner. FIGS. 4, 5 and 6 are liquid chromatograms thereof. As can be seen from FIGS. 4, 5 and 6, G-CSF forms a polymeric micelle type complex with mPEG-PLA-O—SO$_3^-$Na$^+$, but does not form a complex with m-PEG-PLA-OH.

Experiment 2

Figure 7:
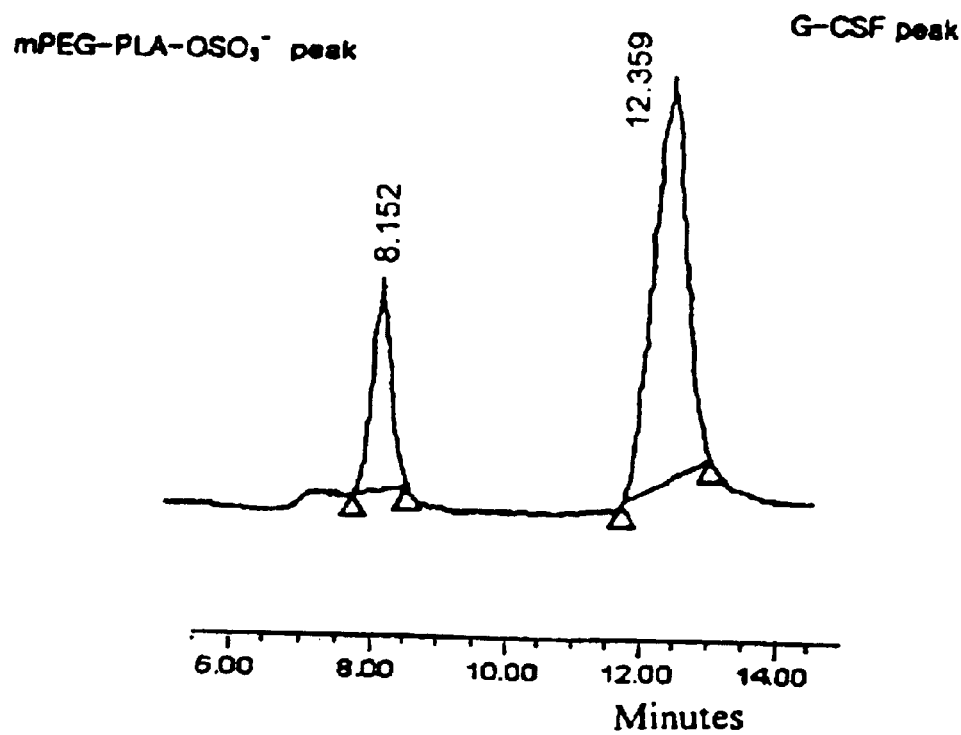
FIG. 7 is a liquid chromatogram of human G-CSF released from mPEG-PLA-O—SO$_3^-$Na$^+$ by size exclusive chromatography.

Confirmation on Whether Drug is Released From the Drug-Polymeric Micelle Type Complex After 75 mg of choline chloride was added to the polymeric micelle type complex solution of Example 17 to facilitate release of G-CSF from the ionic polymeric micelle, the mixture was analyzed by a size exclusive chromatography column (Pharmacia, Superdex HR 75)(injection amount 100 liters, mobile phase pH 7.4 PBS, flow rate 1 ml/min). FIG. 7 is the liquid chromatogram thereof. As confirmed from FIG. 7, since the electrostatic binding between drug and block copolymer is breakable, the drug can be released from the polymeric micelle type complex in a living body. It is also confirmed that the drug is present in an intact state and is not decomposed or coagulated during formation of the drug-block copolymer complex.

Experiment 3

Confirmation on Whether a Drug-Block Copolymer Complex is Formed

Figure 8:
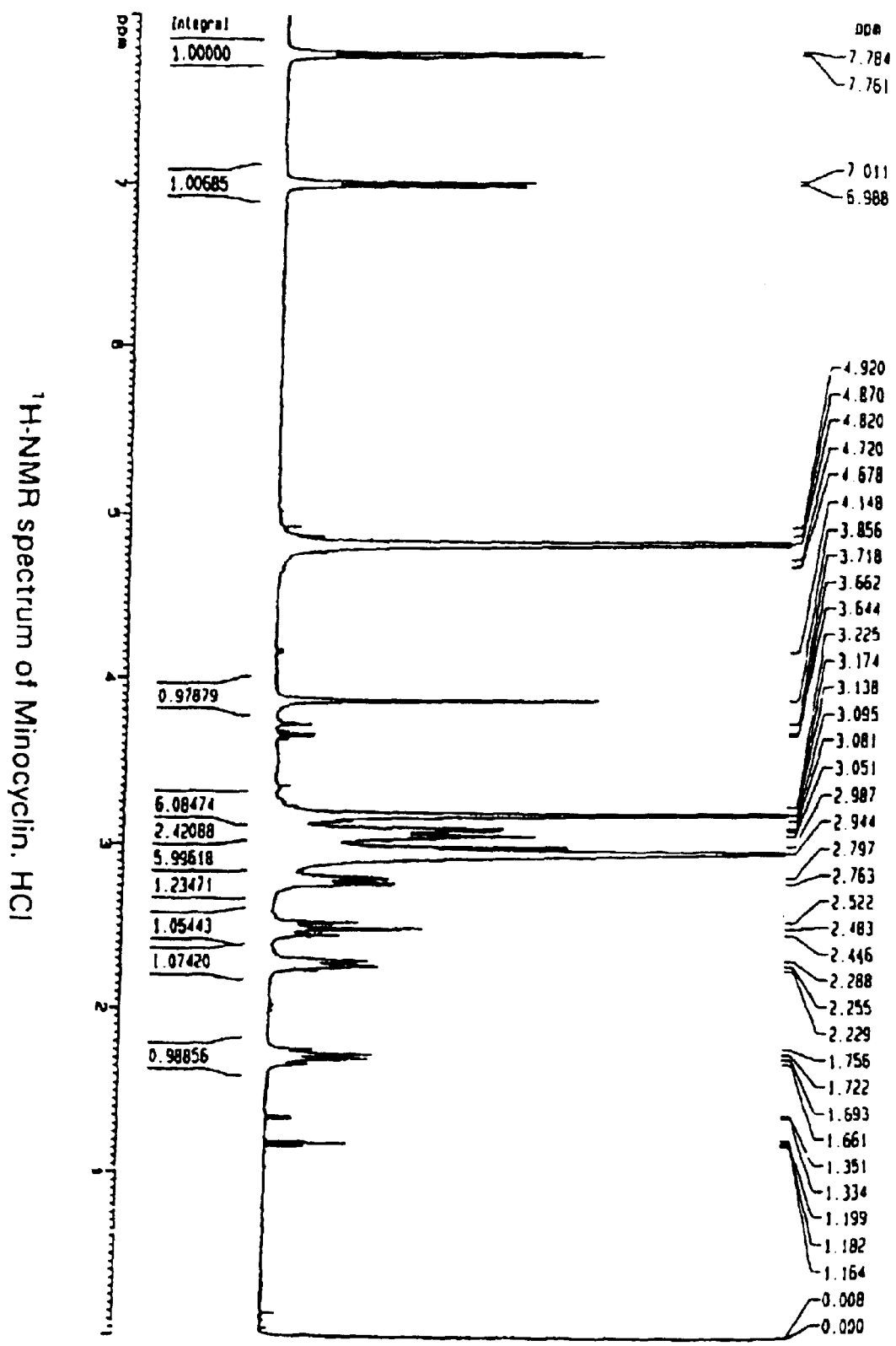
FIG. 8 is an $^1$H-NMR(D$_2$O) spectrum of minocyclin HCl.
Figure 9:
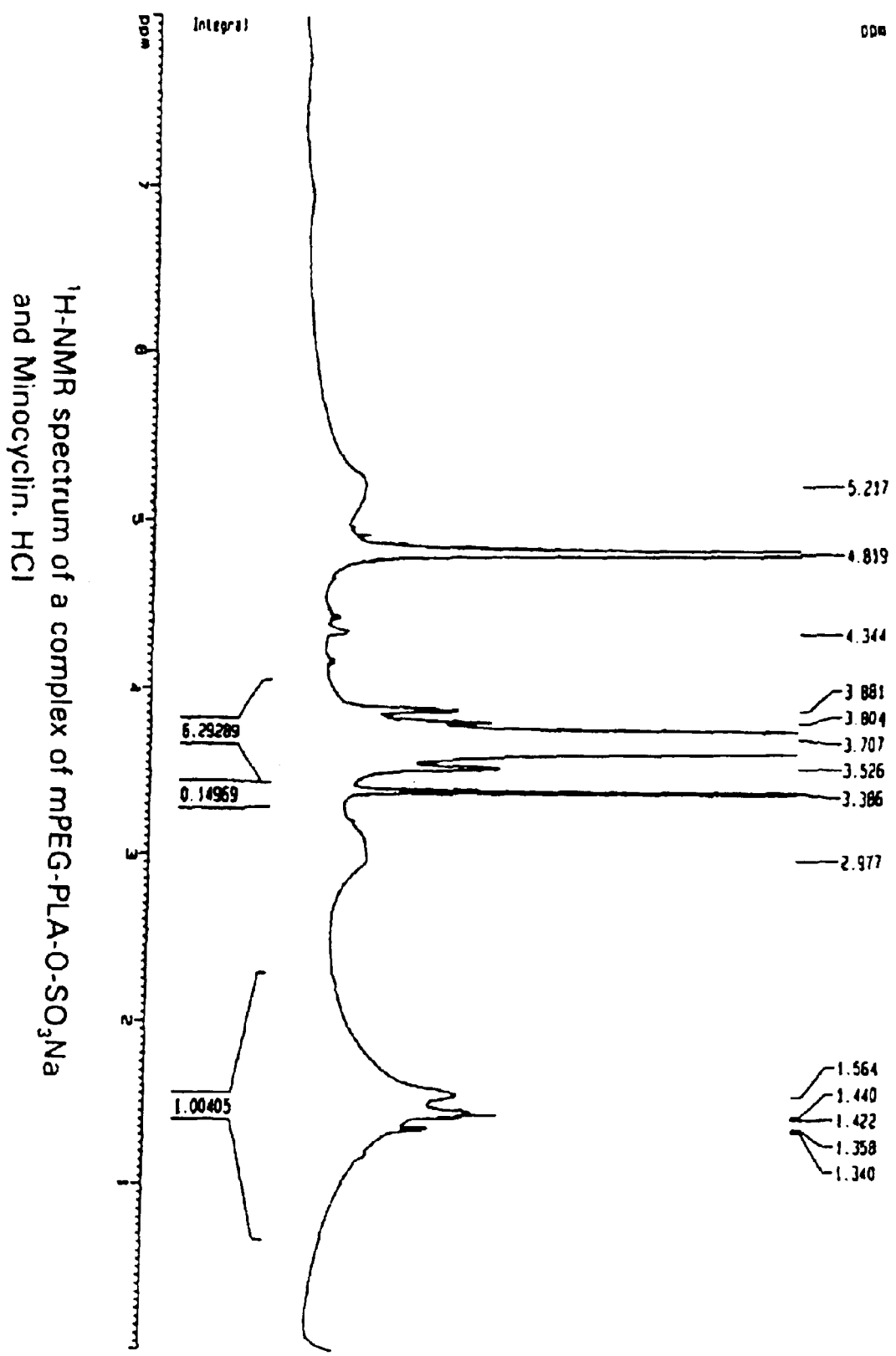
FIG. 9 is an $^1$H-NMR(D$_2$O) spectrum of a complex of minocyclin HCl and mPEG-PLA-O—SO$_3^-$Na$^+$.
Figure 10:
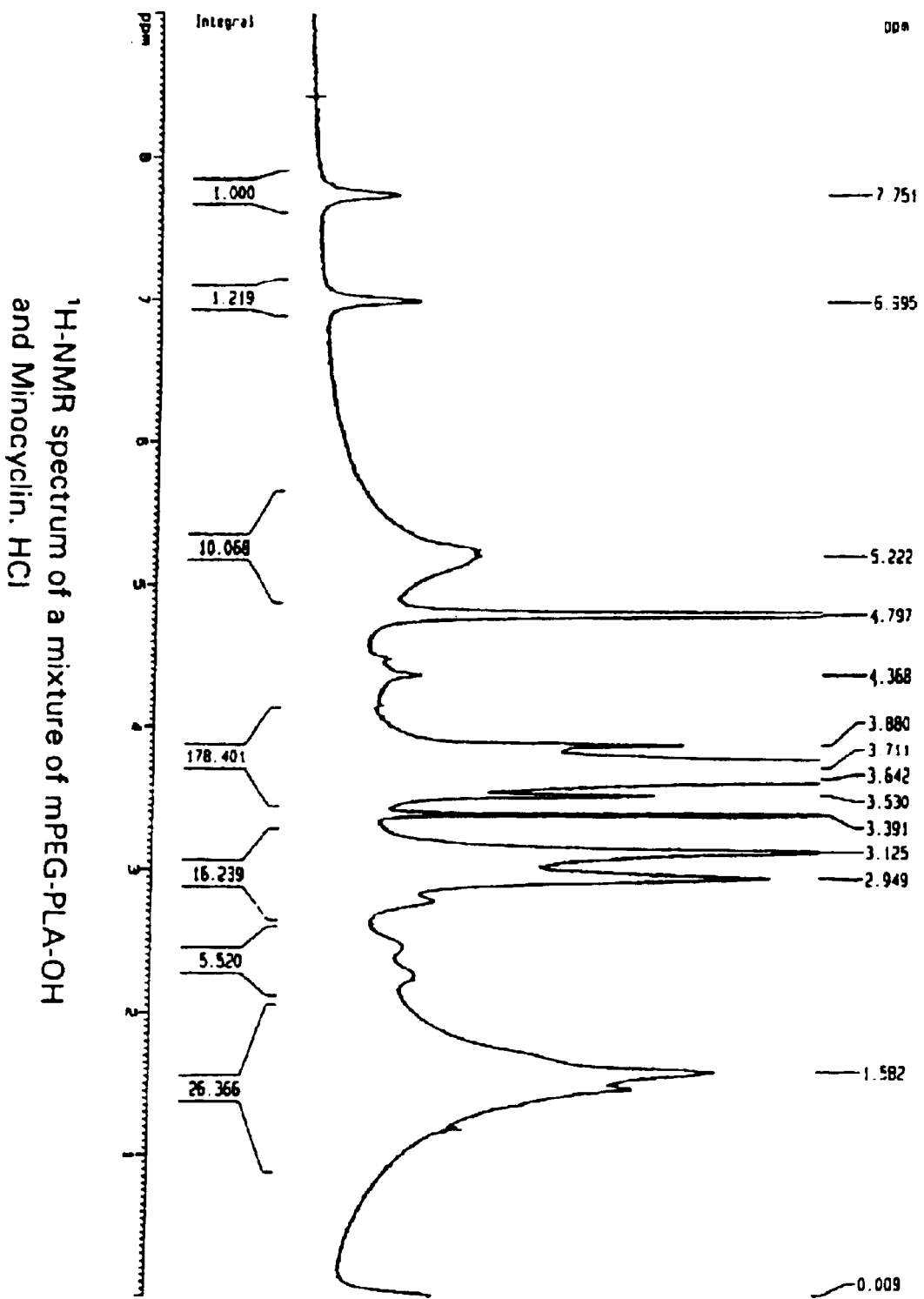
FIG. 10 is an $^1$H-NMR(D$_2$O) spectrum of a mixture of minocyclin HCl and mPEG-PLA-OH.

Minocyclin hydrochloride was dissolved in D$_2$O and then analyzed by NMR spectroscopy. The aqueous solutions obtained in Example 14 and Comparative Example 1 were lyophilized, dissolved in D$_2$O, and then analyzed by NMR spectroscopy. The NMR spectrums are represented in FIGS. 8, 9 and 10. As shown in FIG. 9, in the case of the micelle solution obtained in Example 14, the peak corresponding to H in the aromatic ring of minocyclin disappears completely and only the peak related to polyethyleneglycol is observed. This shows there is incorporation of minocyclin into the block copolymer. To the contrary, as shown in FIG. 10, both peaks corresponding to minocyclin and polyethyleneglycol are observed in the case of the micelle solution obtained in Comparative Example 1, which shows that minocyclin is not incorporated into the non-charged block copolymer.

Experiment 4

Confirmation on Whether a Drug-Block Copolymer Complex is Formed

Figure 11:
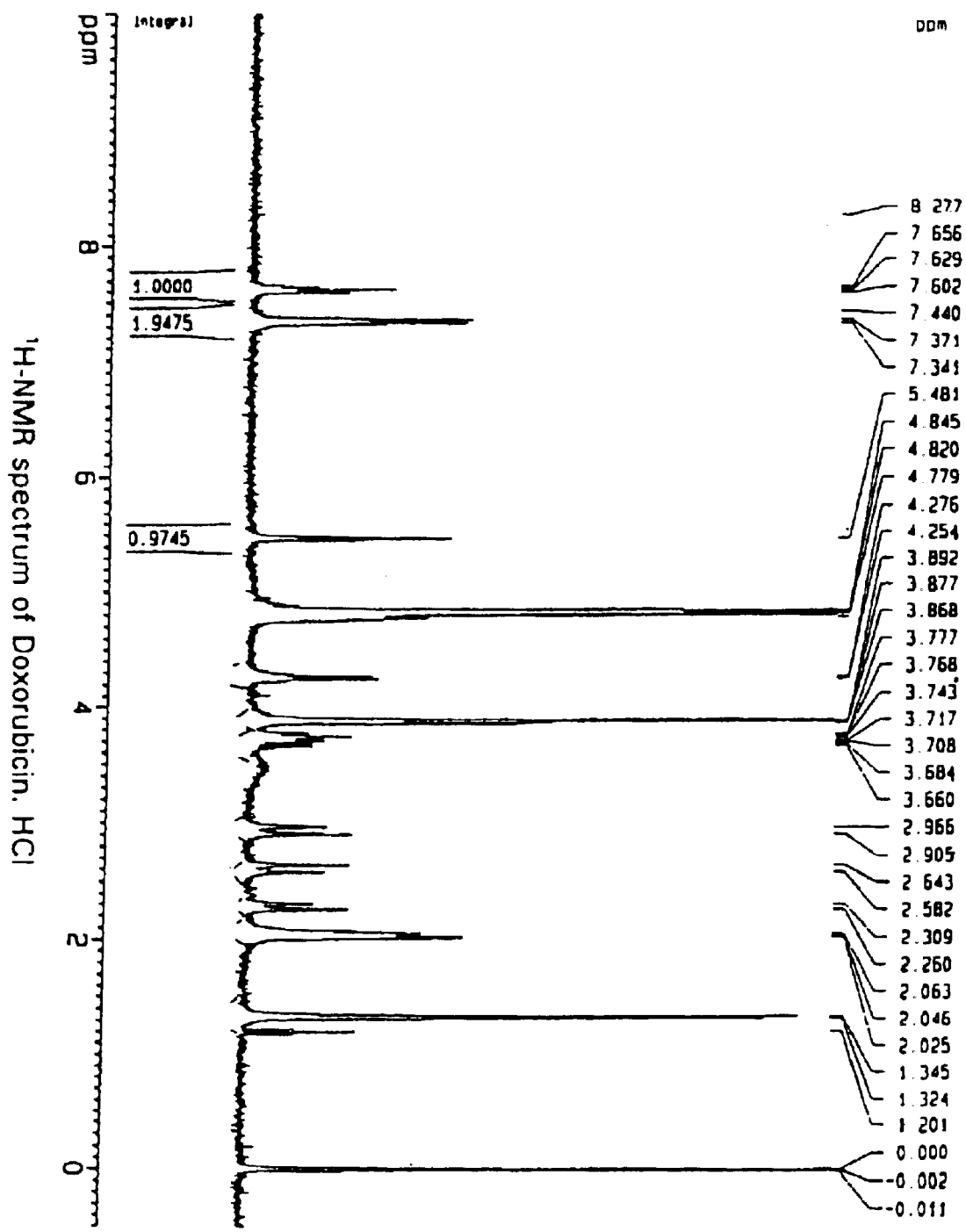
FIG. 11 is an $^1$H-NMR(D$_2$O) spectrum of doxorubicin HCl.
Figure 12:
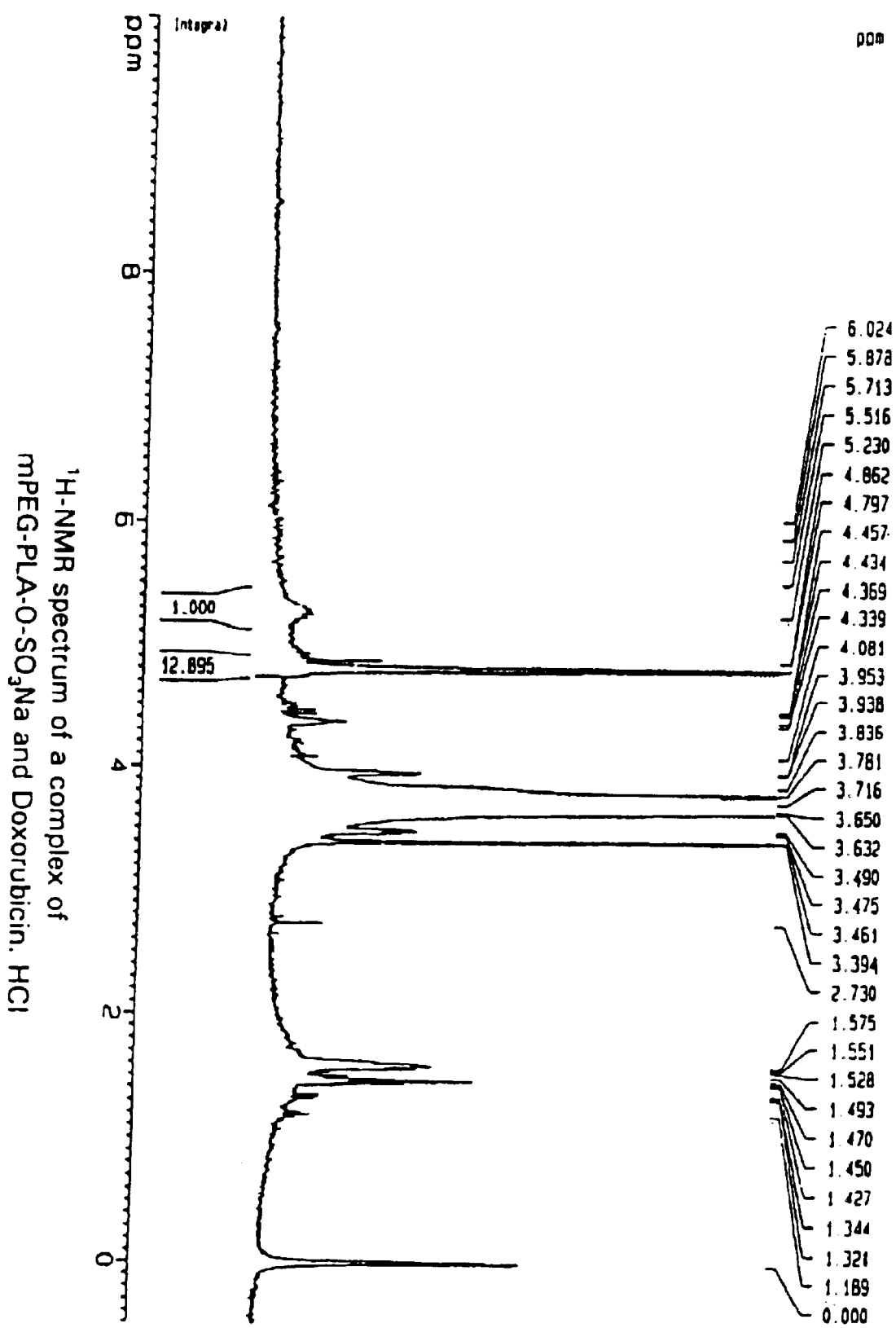
FIG. 12 is an $^1$H-NMR(D$_2$O) spectrum of a complex of doxorubicin HCl and mPEG-PLA-O—SO$_3^-$Na$^+$.

Doxorubicin hydrochloride was dissolved in D$_2$O and then analyzed by NMR spectroscopy. The micelle solution obtained in Example 13 was lyophilized, dissolved in D$_2$O, and then analyzed by NMR spectroscopy. The NMR spectrums are represented in FIGS. 11 and 12. As shown in FIG. 12, in case of the micelle solution obtained in Example 13, the peak corresponding to H in the aromatic ring of doxorubicin disappears completely and only the peak related to polyethyleneglycol is observed. This shows there was incorporation of doxorubicin into the polymeric micelle type complex.

It is to be understood that the above-described embodiments are only illustrative of the applications of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment (s) of the invention, it will be apparent to those of ordinary skill in the art that numerous modifications can be made without departing from the principles and concepts of the invention as set forth in the claims.

What is claim is:

1. A block copolymer having the formula:

$$A\text{-}B\text{-}L\text{-}X\text{-}M^+ \qquad (1)$$

Wherein X represents an anionic group, M$^+$ represents H$^+$ or a metal cation, A is a biocompatible hydrophilic polymer, B is a biodegradable hydrophobic polymer, and L represents a linker selected from the group consisting of —O—, —NH—, —S— and —COO—.

2. The block copolymer of claim 1 wherein the number average molecular weights of A and B each is within the range of 100 to 100,000 Daltons.

3. The block copolymer of claim 1 wherein X is —SO$_3^-$, —PO$_3^-$, =PO$_2^-$ or —CO—(CH$_2$)$_z$—COO$^-$, wherein z denotes an integer of 0 to 4, and if X is =PO$_2^-$, the anionic group is combined with two carbon atoms.

4. The block copolymer of claim 1 wherein M is a mono- or divalent metal ion.

5. The block copolymer of claim 4 wherein M is Li$^+$, Na$^+$, K$^+$, Ca$^{2+}$, Mg$^{2+}$, Zn$^{2+}$ Cu$^{2+}$.

6. A block copolymer having the formula:

$$A\text{-}B\text{-}L\text{-}X\text{-}M^+ \tag{1}$$

Wherein X represents an anionic group, M$^+$ represents H$^+$ or a metal cation, L represents a linker selected from the group consisting of —O—, —NH—, —S— and —COO—, A is a member selected from the group consisting of polyalkyleneglycol, poly-alkyleneoxide, polyvinylpyrrolidone, polysaccharide, polyacrylamide, polymetacrylamide, polyvinylalcohol, and derivatives thereof and B is a biodegradable polyester.

7. The block copolymer of claim 6 wherein the number average molecular weights of A and B each is within the range of 100 to 100,000 Daltons.

8. The block copolymer of claim 6 wherein X is —SO$_3^-$, —PO$_3^{2-}$, =PO$_2^-$ or —CO—(CH$_2$)$_z$—COO$^-$, wherein z denotes an interger of 0 to 4, and if X is =PO$_2^-$, the anionic group is combined with two carbon atoms.

9. The block copolymer of claim 6 wherein M is a mono- or divalent metal ion.

10. The block copolymer of claim 9 wherein M is Li$^+$, Na$^+$, K$^+$, Ca$^{2+}$, Mg$^{2+}$, Zn$^{2+}$ or Cu$^{2+}$.

11. A block copolymer having the formula:

$$A\text{-}B\text{-}L\text{-}X\text{-}M^+ \tag{1}$$

Wherein X represents an anionic group, M$^+$ represents H$^+$ or a metal cation, A is a biocompatible hydrophilic polymer, B is a biodegradable hydrophobic polymer, L represents a linker selected from the group consisting of —O—, —NH—, —S— and —COO—, wherein A is a member selected from the group consisting of polyalkyleneglycol, poly-alkyleneoxide, polyvinylpyrrolidone, a polysaccharide, polyacrylamide, polymetacrylamide, polyvinylalcohol, and derivatives thereof and B is a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, and copolymers thereof.

12. The block copolymer of claim 11 wherein the number average molecular weights of A and B each is within the range of 100 to 100,000 Daltons.

13. The block copolymer of claim 11 wherein X is —SO$_3^-$, —PO$_3^{2-}$, =PO$_2^-$ or —CO—(CH$_2$)$_z$—COO$^-$, wherein z denotes an integer of 0 to 4, and if X is =PO$_2^-$, the anionic group is combined with two carbon atoms.

14. The block copolymer of claim 11 wherein M is a mono- or divalent metal ion.

15. The block copolymer of claim 14 wherein M is Li$^+$, Na$^+$, K$^+$, Ca$^{2+}$, Mg$^{2+}$, Zn$^{2+}$ or Cu$^{2+}$.

16. A block copolymer having the formula:

$$A\text{-}B\text{-}L\text{-}X\text{-}M^+ \tag{1}$$

Wherein X represents an anionic group, M$^+$ represents H$^+$ or a metal cation, A is a biocompatible hydrophilic polymer, B is a biodegradable hydrophobic polymer, L represents a linker selected from the group consisting of —O—, —NH—, —S— and —COO—; and wherein A is a degradable derivative prepared according to the following reaction scheme:

$$nZ + (n-1)Y \rightarrow Z\text{—}(Y\text{—}Z)_{n-2}\text{—}Y\text{—}Z$$

wherein Z represents a water-soluble polymer having a molecular weight of up to 5,000 Daltons, Y represents HOOC—(CH$_2$)$_m$—COOH or O=C=N—(CH$_2$)$_m$—N=C=O wherein m is an integer of 0 to 10, and n is an integer of 2 to 100.

17. The block copolymer of claim 16 wherein the number average molecular weights of A and B each is within the range of 100 to 100,000 Daltons.

18. The block copolymer of claim 16 wherein X is —SO$_3^-$, —PO$_3^{2-}$, PO$_2^-$ or —CO—(CH$_2$)$_z$—COO$^-$, wherein z denotes an interger of 0 to 4, and if X is =PO$_2^-$ the anionic group is combined with two carbon atoms.

19. The block copolymer of claim 16 wherein M is a mono- or divalent metal ion.

20. The block copolymer of claim 19 wherein M is Li$^+$, Na$^+$, K$^+$, Ca$^{2+}$, Mg$^{2+}$, Zn$^{2+}$ or Cu$^{2+}$.

21. A composition comprising the block copolymer of claim 1 and a positively charged drug wherein the positively charged drugs combines with one or more of the block copolymers via electrostatic forces and forms a drug-block copolymer complex.

22. A composition comprising the block copolymer of claim 6 and a positively charged drug wherein the block copolymer combines with one or more of the positively charged drugs via electrostatic forces and forms a drug-block copolymer complex.

23. A composition comprising the block copolymer of claim 11 and a positively charged drug wherein the block copolymer combines with one or more of the positively charged drugs via electrostatic forces and forms a drug-block copolymer complex.

24. A composition comprising the block copolymer of claim 16 and a positively charged drug wherein the block copolymer combines with one or more of the positively charged drugs via electrostatic forces and forms a drug-block copolymer complex.

* * * * *